United States Patent [19]

Shindo et al.

[11] Patent Number: 4,982,312
[45] Date of Patent: Jan. 1, 1991

[54] CHARGE TRANSFER COMPLEX AND SOLID ELECTROLYTIC CAPACITOR EMPLOYING THE SAME

[75] Inventors: Shuko Shindo; Tsuyoshi Aoyama; Yoji Yamaguchi; Isao Isa; Makoto Ebisawa, all of Gunma, Japan

[73] Assignee: The Japan Carlit Co., Ltd., Tokyo, Japan

[21] Appl. No.: 428,231

[22] Filed: Oct. 27, 1989

[30] Foreign Application Priority Data

Oct. 31, 1988 [JP] Japan .................................. 63-273104
Oct. 31, 1988 [JP] Japan .................................. 63-273105

[51] Int. Cl.$^5$ ............................................. H01G 9/05
[52] U.S. Cl. ..................................... 361/527; 252/62.2
[58] Field of Search ............... 361/523, 524, 525, 527; 29/570.1; 252/62.2, 500

[56] References Cited

U.S. PATENT DOCUMENTS 4,688,153  8/1987  Ebisawa et al. ...................... 361/527
4,729,844  3/1988  Tsuchiya et al. .................... 361/527
4,735,823  4/1988  Ito et al. .......................... 361/527 X

FOREIGN PATENT DOCUMENTS 17609    2/1983  Japan .
191414  11/1983  Japan .
116552   5/1987  Japan .

Primary Examiner—Donald A. Griffin
Attorney, Agent, or Firm—Fitch, Even, Tabin and Flannery

[57] ABSTRACT

A charge transfer complex comprising N,N'-alkylene-di-3,5-lutidine as a donor and 7,7,8,8-tetracyanoquinodimethane as an acceptor, the molar ratio of the acceptor to the donor of the charge transfer complex being between 3.0 and 5.0 has a high melting point and excellent electrical conductivity as an electrolyte for a capacitor. A solid electrolytic capacitor employing said charge transfer complex has reduced current leakage and high temperature load characteristics. A chip-type solid electrolytic capacitor employing said charge transfer complex has reduced current leakage, high temperature load characteristics and excellent thermal stability and life characteristics.

9 Claims, 13 Drawing Sheets

CHARGE TRANSFER COMPLEX AND SOLID ELECTROLYTIC CAPACITOR EMPLOYING THE SAME

BACKGROUND OF THE INVENTION

1. Field of the Invention

The present invention relates to a novel organic charge transfer complex which has a high melting point, a solid electrolytic capacitor employing the same, and to a process for the preparation thereof. The present invention also pertains to a chip-type solid electrolytic capacitor employing said charge transfer complex.

2. Description of the Related Art

The development of digital devices in recent years has given rise to a demand for smaller size capacitors having a large-capacity which also have excellent high-frequency characteristics, and for chip-type capacitors which are indispensable in surface mounting on a printed wiring circuit.

Electrolytic capacitors mass produced by conventional methods and, which are known to have a large-capacity, include two types, the liquid electrolyte type in which a liquid electrolyte is impregnated, and the solid electrolyte type in which manganese dioxide is employed as a solid electrolyte. The former type of electrolytic capacitor utilizes ion conduction, and therefore resistance remarkably increases in the high frequency region with a corresponding disadvantageous increase in impedance, moreover this capacitor cannot be surface mounted by a soldering process. The latter type of electrolytic capacitor also has relatively high impedance in the high-frequency region partly because manganese dioxide has a relatively high specific resistance. Since this capacitor was subjected to thermal decomposition to obtain manganese dioxide from manganese nitrate, the oxide of film-forming aluminum electrode thereof was readily damaged, so that the leakage current of the capacitor remarkably increased.

In order to overcome the above-described disadvantages of conventional capacitors, one type of electrolytic capacitor which employs as a solid electrolyte a charge transfer complex consisting of a combination of 7,7,8,8-tetracyanoquinodimethane (hereinafter referred to as TCNQ) and a donor has already been proposed.

Examples of the donor employed in the proposed TCNQ charge transfer complex include N-n-hexylquinoline, N-ethylisoquinoline, N-n-butylisoquinoline (see Japanese Patent Public Disclosure No. 191414/1983), N-n-amylisoquinoline, N-isoamylisoquinoline (see Japanese Patent Public Disclosure No. 116552/1987), N-n-propylisoquinoline and N-isopropylisoquinoline (see Japanese Patent Public Disclosure No. 17609/1983).

However, the conventional TCNQ charge transfer complex which may be composed of the above-described compounds suffers from an inferior thermal stability and therefore melts or decomposes during the soldering process of surface mounting to become an insulator. Moreover a leakage current of a capacitor employing the conventional complex increases to a great extent during the soldering process because the oxide film is damaged. This prior art is also unsatisfactory in the manufacture of chip-type solid electrolytic capacitors.

SUMMARY OF THE INVENTION

It is therefore an object of the present invention to provide a charge transfer complex comprising N,N'-alkylene-di-3,5-lutidine as a donor and 7,7,8,8-tetracyanoquinodimethane as acceptor which has a high melting point and excellent electrical conductivity as an electrolyte for capacitor.

Another object of the present invention is to provide a solid electrolytic capacitor employing the charge transfer complex above-mentioned, said capacitor having reduced current leakage and high temperature load characteristics.

Still another object of the present invention is to provide a chip-type solid electrolytic capacitor employing the charge transfer complex above-mentioned, said capacitor having reduced current leakage, high temperature load characteristics and excellent thermal stability and life characteristics.

Other objects and advantages of the present invention will become apparent to those skilled in the art from the following description and drawings.

Figure 1:
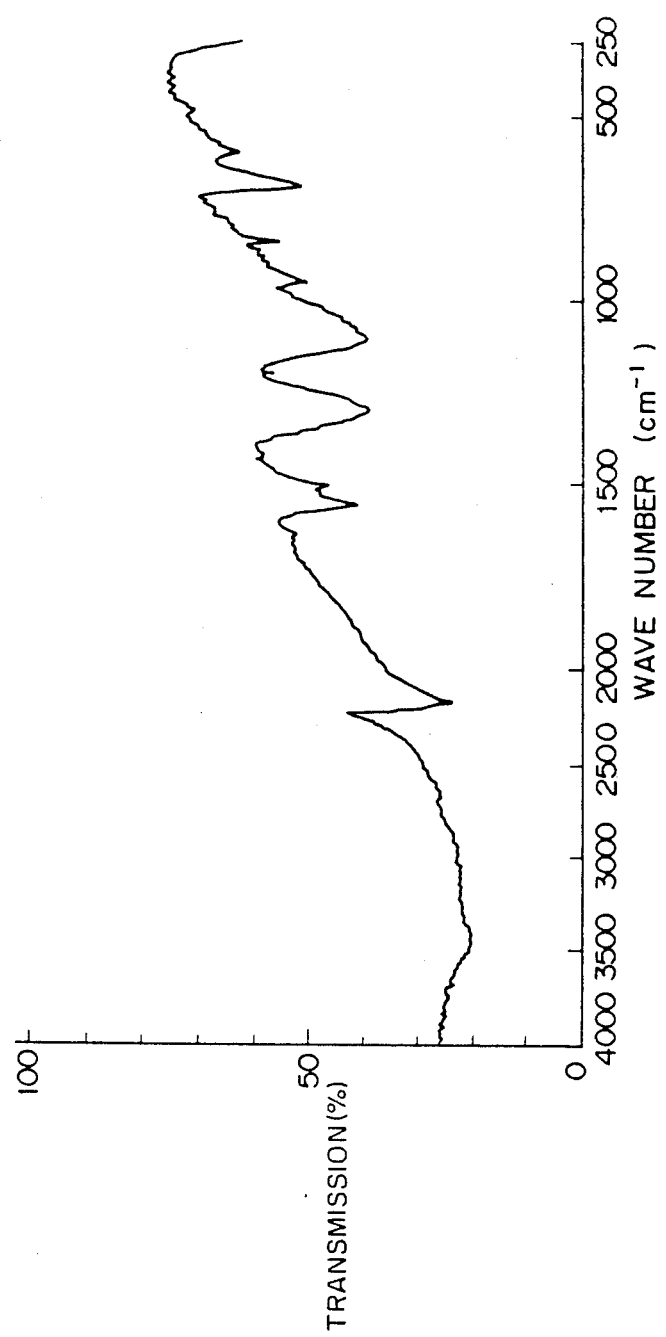
FIG. 1 shows an infra-red spectrum of the charge transfer complex of N,N'-pentamethylene-di-3,5-lutidinium TCNQ obtained in Example 1.

DETAILED DESCRIPTION OF THE PREFERRED EMBODIMENT:

The present inventors have found that the above-described disadvantages of the prior art can be overcome by a charge transfer complex comprising N,N'-alkylene-di-3,5-lutidine as a donor and TCNQ as an acceptor, and by adopting this solid electrolyte having a high melting point and high decomposing point at excellent (chip-type) solid electrolytic capacitor was attained.

The present invention has been accomplished on the basis of this finding.

Examples of N,N'-alkylene-di-3,5-lutidine as donor employed in the present invention is depicted in the following formula,

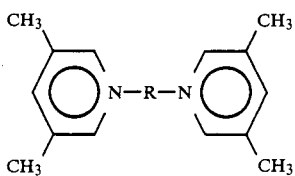

where the number of carbon atoms of alkylene, R, is between 1 and 12.

Although the molar ratio of the acceptor to the donor of generally known charge transfer complexes is 1 or 2, the molar ratio of TCNQ to an N,N'-alkylene-di-3,5-lutidine of the complex according to the present invention should be between 3.0 and 5.0, preferably between 3.5 and 4.5. The molar ratio of the complex is controlled by the molar ratio of the reactants.

The following is a description of the process for synthesizing the charge transfer complex according to the present invention.

Corresponding alkylenediiodide and 3,5-lutidine are reacted with each other at a temperature between room temperature and a reflux temperature in an organic solvent or in no solvent under a pressure of 0.2 to 2 kg/cm$^2$ to introduce the alkylenediiodide to the N-positions of the corresponding bridged 3,5-lutidine as a donor. Among said organic solvents, acetonitrile and an alcoholic solvent are particularly preferable. Then this diiodide of the donor and TCNQ are reacted with each other in an organic solvent, preferably acetonitrile, at a temperature between room temperature and a reflux temperature under a pressure of 0.2 to 2 kg/cm$^2$ to obtain the charge transfer complex according to the present invention.

The thus obtained charge transfer complex of the present invention is dissolved into an organic solvent to prepare an impregnating solution, and an anode material is dipped in the solution to be impregnated therewith. Thereafter, the organic solvent is evaporated to form a complex layer on the surface of the anode material, thereby obtaining a capacitor unit.

Alternatively, a melted charge transfer complex is impregnated into a capacitor unit consisting of aluminum anode having anodized surface on the etched aluminum plate, aluminum cathode and spacer between them, and is then cooled to obtain a capacitor unit having the complex attached thereto, this impregnated capacitor unit being incorporated into a casing member or the like to obtain a solid electrolytic capacitor. The spacer such as separating paper and separating fiber sustains the complex between two electrodes and prevents them from touching themselves.

Among the charge transfer complexes of the present invention, which comprises an N,N'-alkylene-di-3,5-lutidine as a donor and TCNQ as an acceptor, the charge transfer complexes wherein the number of carbon atoms of alkylene is between 5 and 8 are particularly preferable in terms of thermal stability and electroconductivity compared with the conventional charge transfer complexes. That is, the said charge transfer complexes have a high melting point in excess of 230° C. and also have a high decomposing point, so the solid electrolytic capacitor wherein the said complex is adopted as a solid electrolyte can be applied in the soldering process of both the flow method and reflow method. In particular, a chip-type solid electrolytic capacitor is obtained by using the said charge transfer complexes which was impossible for the conventional charge transfer complexes largely because of its low melting point. The heating temperature of said complex and the capacitor unit in the procedure of impregnation is between 310° C. and 345° C.

Furthermore, the charge transfer complex of the present invention can be advantageously put to practical use in many fields as a material capable of imparting electrical conductivity to polymers, semiconductor devices, anode active materials for batteries, antistatic agents, heat sensitive materials, photoconductive materials, display devices, electrostatic recording, etc.

Figure 11:
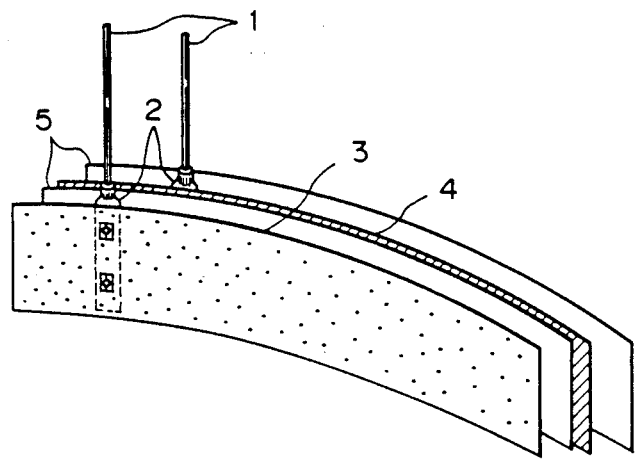
FIG. 11 is a schematic, partial view illustrating the structure of a capacitor unit before winding to be used in the present invention.
Figure 12:
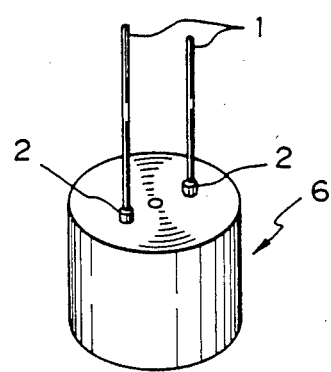
FIG. 12 is a schematic, partial view illustrating the external appearance of a capacitor unit after winding to be used in the present invention.
Figure 13:
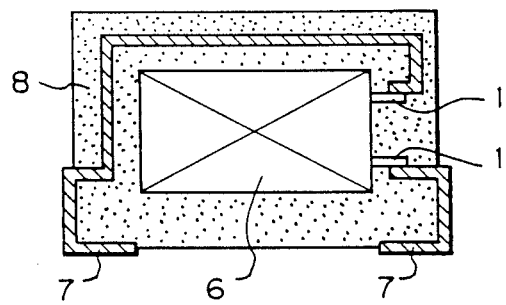
FIGS. 13–19 are schematic, sectional views of various forms of the structure of a chip-type solid electrolytic capacitor unit of the present invention.
Figure 14:
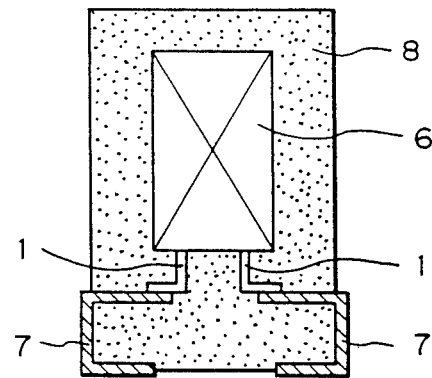
Figure 15:
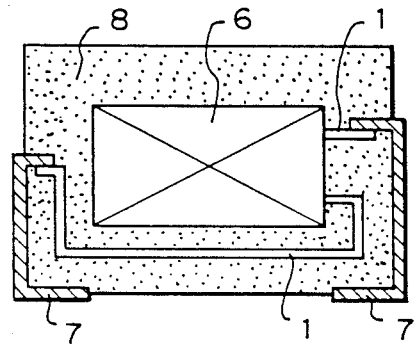

In FIGS. 11-12, the numeral 1 indicates a lead wire which is extended from aluminum boss 2 and two aluminum bosses are attached to respective aluminum anode 3 and aluminum cathode 4. Spacer 5 is placed between aluminum anode 3 and aluminum cathode 4. Capacitor unit 6 comprises aluminum anode 3, aluminum cathode 4 and spacer 5. In FIGS. 13-15, capacitor unit 6 is impregnated with a charge transfer complex of the present invention, extended electrode end 7 is connected to lead wire 1 and capacitor unit 6 is sealed with sealing resin 8. In FIGS. 16-19, capacitor unit 6 is placed into aluminum case 9 in addition to ones of FIGS. 13-15, and further, in FIG. 19, heat-resisting resin 10 is placed under capacitor unit 6 without having extended electrode end 7.

The present invention will be explained more specifically below by way of Examples. However, the present invention is in no way to be taken as being restricted to those Examples.

EXAMPLE 1

To 2.14 g of 3,5-lutidine placed in a four-necked flask equipped with a reflux condenser and mechanical stirrer was added 3.24 g of pentamethylenediiodide dissolved in 5 ml of acetonitrile. The mixture was reacted for one hour under reflux. When the reaction was completed, acetonitrile was removed from the reaction mixture under reduced pressure, the residue was washed 2 times with 30 ml of ethyl ether. 5.29 g of N,N'-pentamethylene-di-3,5-lutidinium diiodide was obtained as yellowish white crystals. Subsequently, into a four-necked flask equipped with a reflux condenser and mechanical stirrer was placed 4.25 g of TCNQ and 120 ml of acetonitrile under reflux. To the flask was added a solution of 4.20 g of N,N'-pentamethylene-di-3,5-lutidinium diiodide in 40 ml of acetonitrile. The mixture was reacted for 30 minutes under reflux. The reaction mixture was cooled to 10° C., and precipitated black needles were filtered out and washed 2 times with 50 ml of methanol.

5.33 g of charge transfer complex of N,N'-pentamethylene-di-3,5-lutidinium TCNQ was obtained. The infrared spectrum of the complex is shown in FIG. 1.

The results of an elemental analysis of the complex was as follows:

Elemental analysis: $C_{67}H_{44}N_{18}$. Found: C 73.14; H 4.01; N 22.85 (%). Calculated: C 73.08; H 4.03; N 22.89 (%).

The molar ratio of TCNQ to an N,N'-pentamethylene-di3,5-lutidine was to be 4 from the above data.

Figure 2:
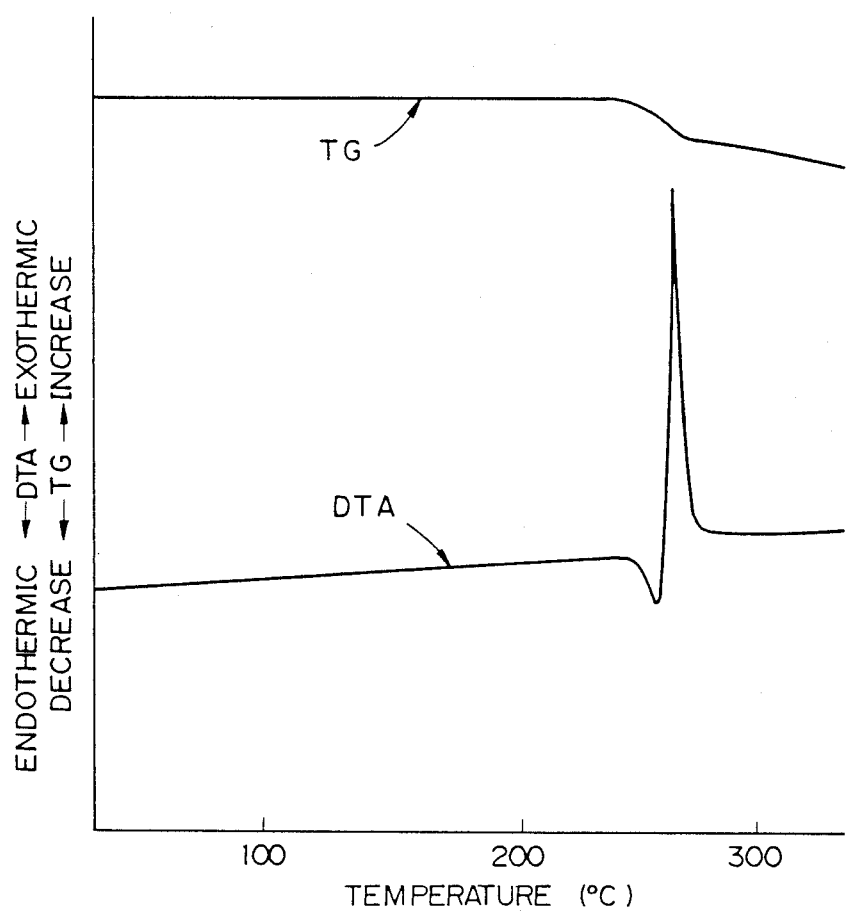
FIG. 2 shows the measurement results of thermogravimetry (TG) and differential thermal analysis (DTA) of the charge transfer complex of N,N'-pentamethylene-di-3,5-lutidinium TCNQ obtained in Example 1.

And the results of thermogravimetry (TG) and differential thermal analysis (DTA) are shown in FIG. 2. The measurements of TG and DTA were carried out using 5.7 mg of a sample in an open aluminum case at a heating rate of 15° C./min. under ambient pressure.

As shown in FIG. 2, the melting point of the charge transfer complex of N,N'-pentamethylene-di-3,5-lutidinium TCNQ was 247° C., and the exothermic decomposition temperature was 263° C.

EXAMPLE 2

Figure 3:
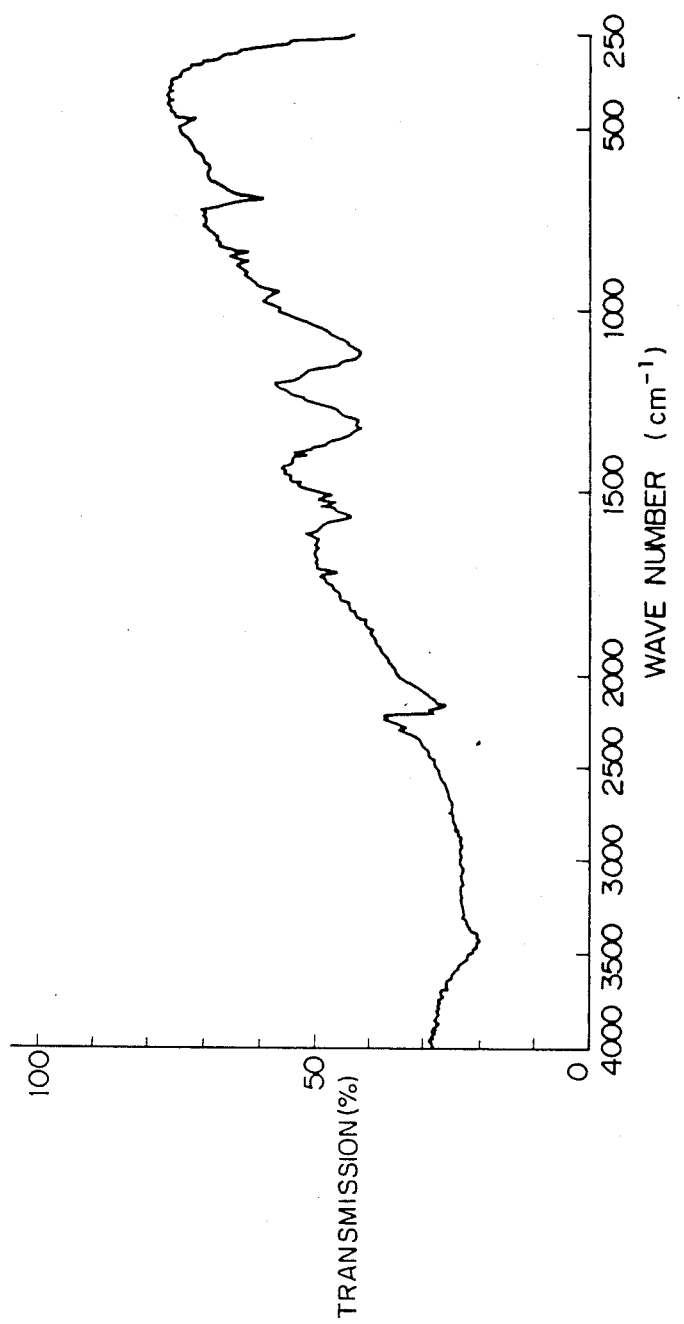
FIG. 3 shows an infra-red spectrum of the charge transfer complex of N,N'-1,3-dimethyltrimethylene-di-3,5-lutidinium TCNQ obtained in Example 2.
Figure 4:
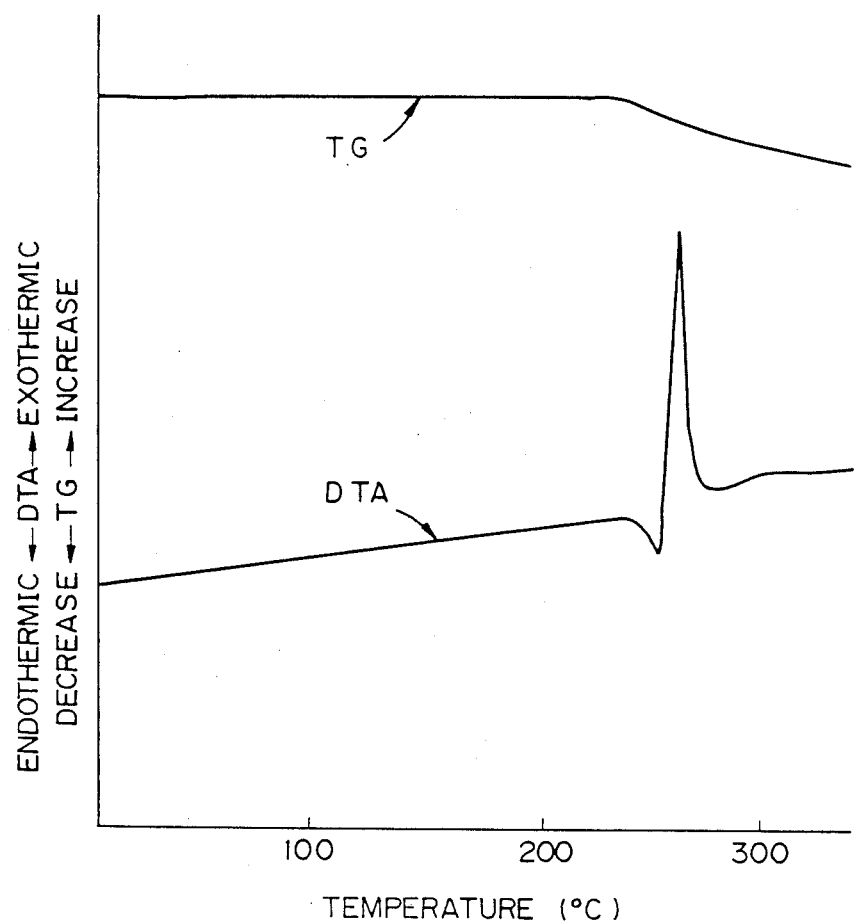
FIG. 4 shows the measurement results of TG and DTA of the charge transfer complex of N,N'-1,3-dimethyltrimethylene-di-3,5-lutidinium TCNQ obtained in Example 2.

N,N'-1,3-dimethyltrimethylene-di-3,5-lutidinium TCNQ complex was prepared in accordance with Example 1 except that pentamethylenediiodide was replaced by 2,4-diiode-n-pentane. The infra-red spectrum of the complex is shown in FIG. 3. The measurements of TG and DTA were carried out by the same methods as those described in Example 1. The results of TG and DTA are shown in FIG. 4 and in Table 1.

EXAMPLE 3

Figure 5:
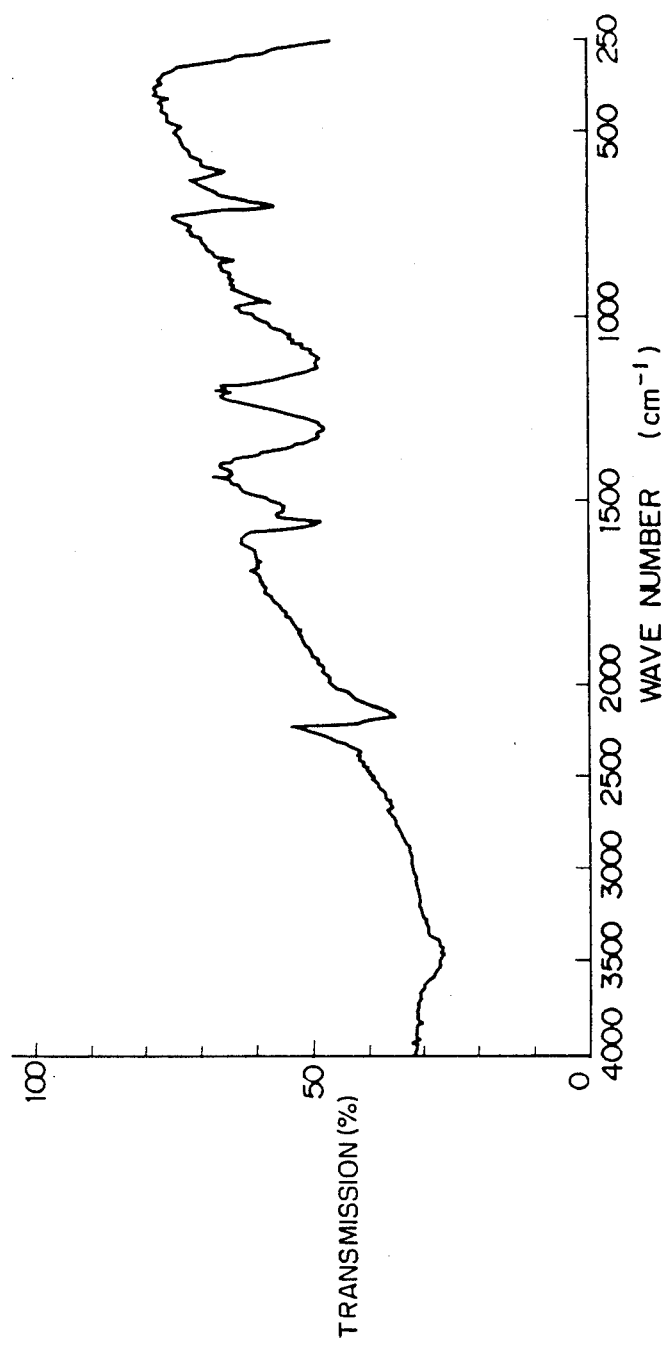
FIG. 5 shows an infra-red spectrum of the charge transfer complex of N,N'-hexamethylene-di-3,5-lutidinium TCNQ obtained in Example 3.
Figure 6:
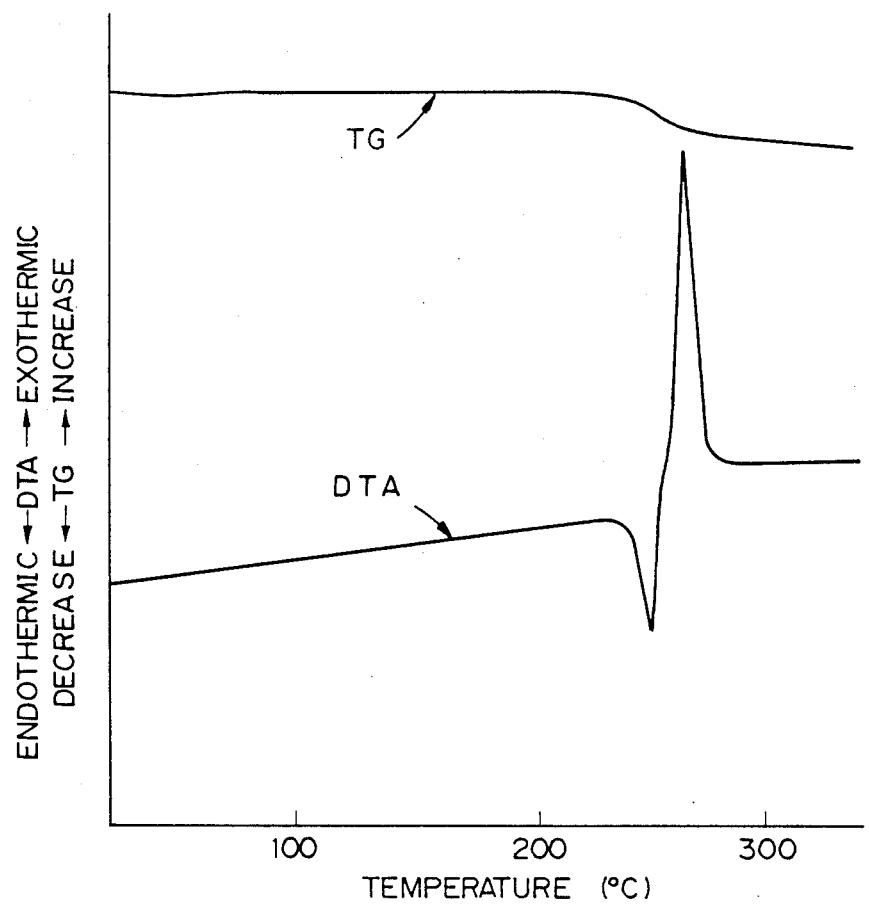
FIG. 6 shows the measurement results of TG and DTA of the charge transfer complex of N,N'-hexamethylene-di-3,5-lutidinium TCNQ obtained in Example 3.

N,N'-hexamethylene-di-3,5-lutidinium TCNQ complex was prepared in accordance with Example 1 except that pentamethylenediiodide was replaced by hexamethylenediiodide. The infra-red spectrum of the complex is shown in FIG. 5. The measurements of TG and DTA were carried out by the same methods as those described in Example 1. The results of TG and DTA are shown in FIG. 6 and in Table 1.

EXAMPLE 4

Figure 7:
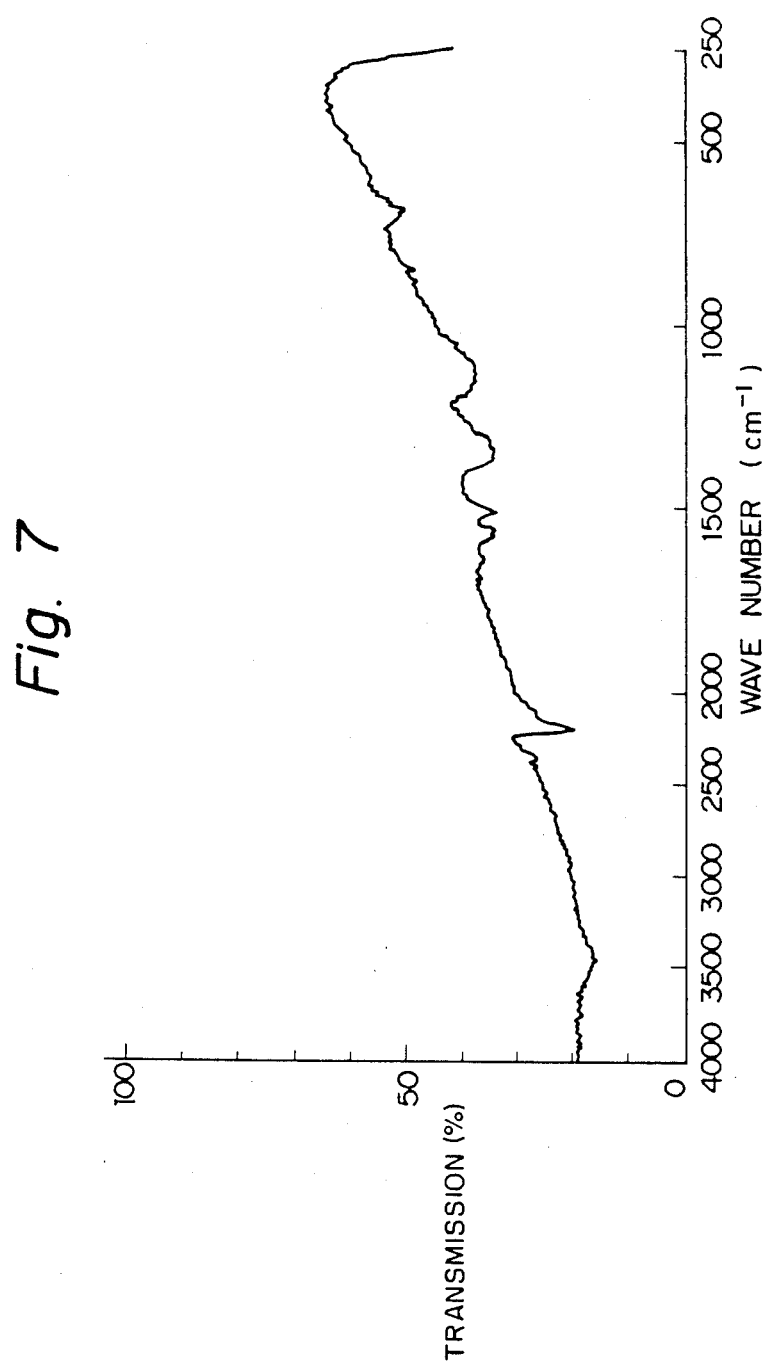
FIG. 7 shows an infra-red spectrum of the charge transfer complex of N,N'-octamethylene-di-3,5-lutidinium TCNQ obtained in Example 4.
Figure 8:
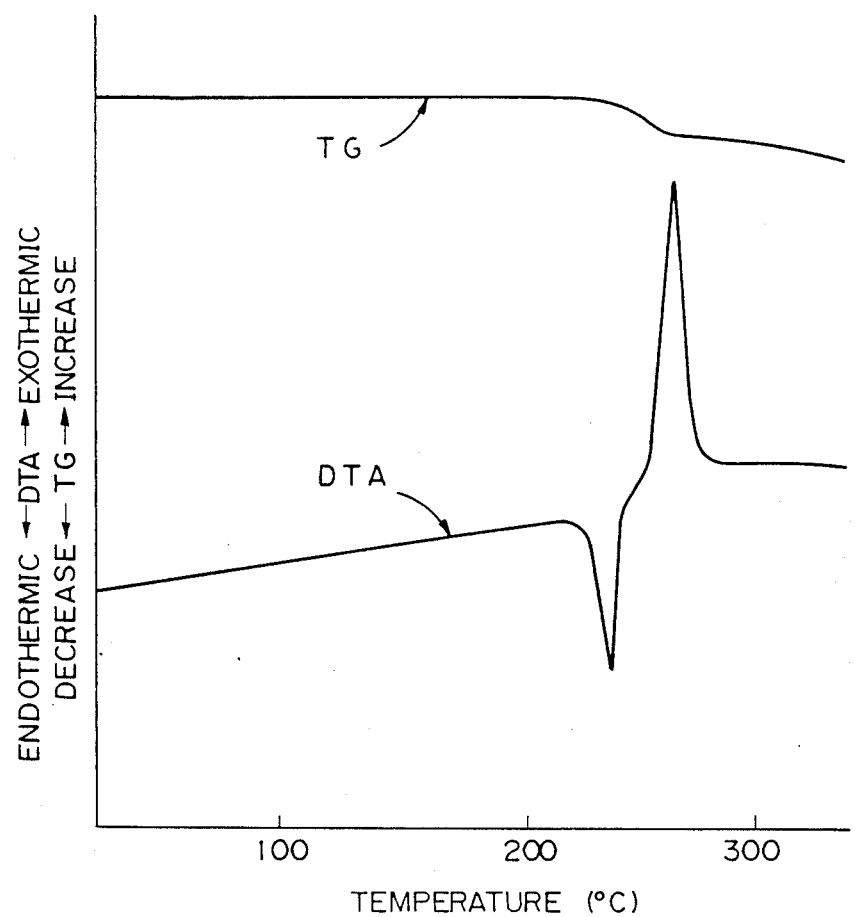
FIG. 8 shows the measurement results of TG and DTA of the charge transfer complex of N,N'-octamethylene-di-3,5-lutidinium TCNQ obtained in Example 4.

N,N'-octamethylene-di-3,5-lutidinium TCNQ complex was prepared in accordance with Example 1 except that pentamethylenediiodide was replaced by octamethylenediiodide. The infra-red spectrum of the complex is shown in FIG. 7. The measurements of TG and DTA were carried out by the same methods as those described in Example 1. The results of TG and DTA are shown in FIG. 8 and in Table 1.

COMPARATIVE EXAMPLE 1

Figure 9:
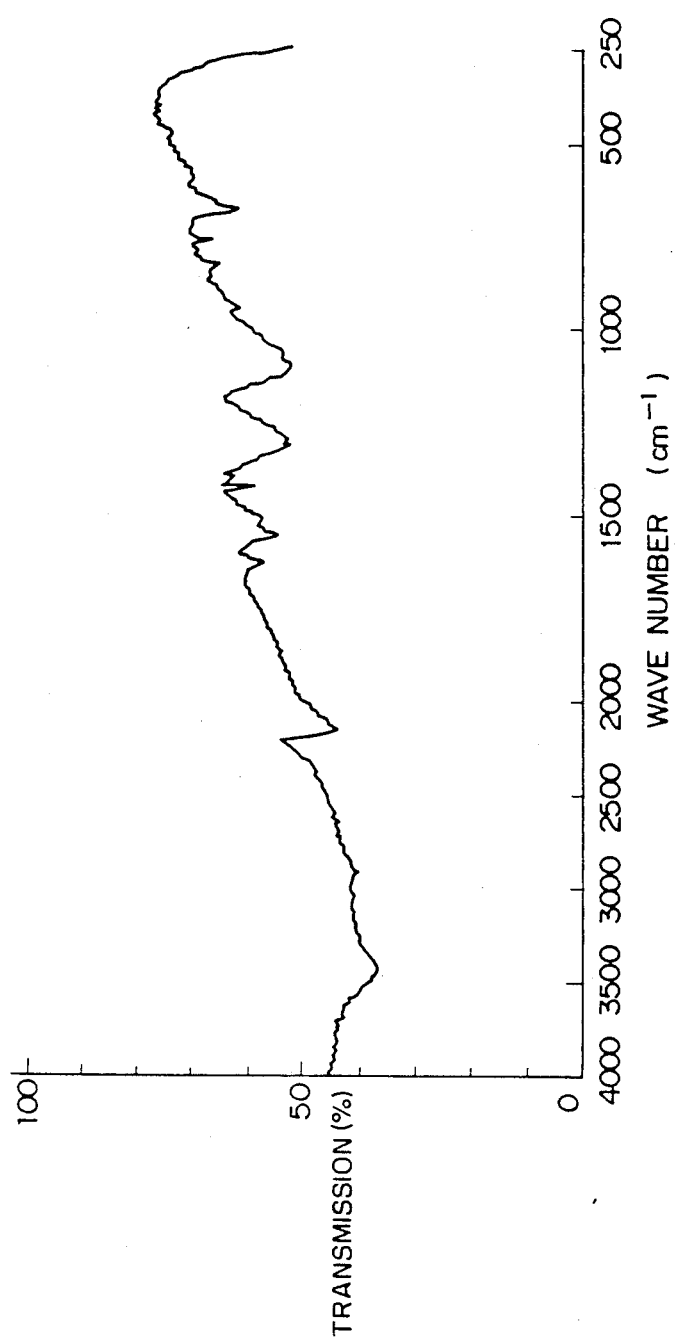
FIG. 9 shows an infra-red spectrum of a conventional charge transfer complex, N-n-butylquinolinium TCNQ.
Figure 10:
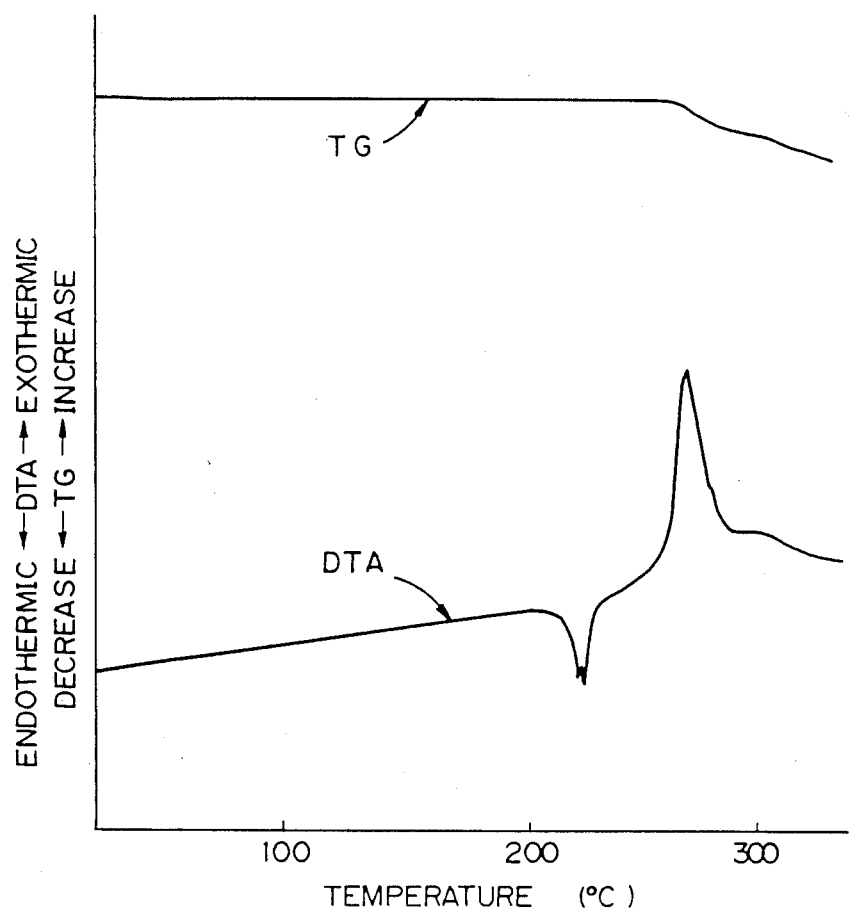
FIG. 10 shows the measurement results of TG and DTA of the conventional charge transfer complex, N-n-butylquinolinium TCNQ.

To 1.29 g of quinolinium was added 1.84 g of n-butyliodide dissolved in 3 ml of acetonitrile in accordance with Example 1. Subsequently, corresponding iodide was obtained, then N-n-butylquinolinium TCNQ complex was prepared. The infra-red spectrum of the complex is shown in FIG. 9. The measurements of TG and DTA were carried out by the same methods as those described in Example 1. The results of TG and DTA are shown in FIG. 10 and in Table 1.

TABLE 1

| Donor of complex | Melting point (°C.) | Exothermic decomposition temperature (°C) |
|---|---|---|
| Ex. 1 | N,N'-pentamethylene-di-3,5-lutidinium | 247 | 263 |
| Ex. 2 | N,N'-1,3-dimethyltrimethylene-di-3,5-lutidinium | 242 | 261 |
| Ex. 3 | N,N'-hexamethylene-di-3,5-lutidinium | 237 | 260 |
| Ex. 4 | N,N'-octamethylene-di-3,5-lutidinium | 230 | 256 |
| Comp. Ex. 1 | N-n-butylquinolinium | 215 | 228 |

The thermal properties of charge transfer complexes consisting of bridged 3,5-lutidinium with alkylene, the number of carbon atoms of which varied from 5 to 8 are summarized in Table 1. This table indicates that complexes containing bridged 3,5-lutidinium as a donor have a melting point of 230° C. or more and a high decomposition point.

EXAMPLE 5

Into an aluminum case (6.3 mmφ) was charged 60 mg of the complex obtained in Example 1, and this was heated at a temperature of 340° C. to melt. A winding type aluminum electrolytic capacitor unit comprising an aluminum anode having anodized surface on the etched aluminum plate, an aluminum cathode and separating paper (see FIGS. 11 and 12) was then impregnated with the melted complex at 340° C. and immediately cooled to obtain a solid electrolytic capacitor. This capacitor unit was also preheated to 340° C. before impregnation. The rated voltage and rated capacitance of this unit were 16 V and 15 μF respectively. After sealing with a resin, the leakage current of this capacitor was reduced by applying the voltage of 16 V at 105° C. The characteristics of the capacitor obtained are shown in Table 2, and also shown are the high temperature load characteristics of this capacitor after being subjected to a temperature of 105° C. for 1000 hours.

EXAMPLE 6

The experiment of Example 5 was repeated except that the complex obtained in Example 1 was replaced by that obtained in Example 4. The characteristics of the capacitor are shown in Table 2.

COMPARATIVE EXAMPLE 2

The experiment of Example 5 was repeated except that the complex obtained in Example 1 was replaced by N-n-propylisoquinolinium TCNQ complex prepared by the method in accordance with Comparative Example 1 and that heating temperature of 340° C. for the complex and capacitor unit was replaced by 290° C. The characteristics of the capacitor are shown in Table 2.

TABLE 2

| | Initial value | | | Value after 1000 hours at 105° C. | | |
|---|---|---|---|---|---|---|
| | Cap (μF) | tan δ (%) | LC/60" (μA) | Cap (μF) | tan δ (%) | LC/60" (μA) |
| Example 5 | 15.71 | 1.93 | 0.02 | 15.20 | 1.97 | 0.02 |
| Example 6 | 15.70 | 2.14 | 0.02 | 15.29 | 2.21 | 0.02 |
| Comparative Example 2 | 15.67 | 2.78 | 0.02 | 14.16 | 3.59 | 0.13 |

In Table 2, Cap means electrostatic capacitance at 120 Hz, tan δ means dielectric loss tangent at 120 Hz, LC/60" means leakage current applied at 16 V for 60 seconds. And each value is the average obtained for 10 samples.

As shown in Table 2, the characteristics of the capacitor of the present invention are superior to those of the Comparative Example 2, especially the high temperature load characteristics, this implies that the capacitor of the present invention has excellent thermal stability and life characteristics.

EXAMPLE 7

Into the solder bath maintained at 260° C. was dipped the capacitor prepared by the same procedure to Example 5 for 10 seconds. The characteristics of the capacitor before and after subjection to the test are shown in Table 3.

EXAMPLE 8

The experiment of Example 7 was repeated for the capacitor prepared by the same procedure as in Example 6. The characteristics of the capacitor before and after subjection to the test are shown in Table 3.

COMPARATIVE EXAMPLE 3

The experiment of Example 7 was repeated for the capacitor prepared by the same procedure at the Comparative Example 2. The characteristics of the capacitor before and after subjection to the test are shown in Table 3.

TABLE 3

| | Initial value | | | | Value after soldering test | | | |
|---|---|---|---|---|---|---|---|---|
| | Cap (μF) | tan δ (%) | ESR (mΩ) | LC/60" (μA) | Cap (μF) | tan δ (%) | ESR (mΩ) | LC/60" (μA) |
| Ex. 7 | 15.70 | 1.94 | 132 | 0.02 | 15.82 | 1.98 | 131 | 0.02 |
| Ex. 8 | 15.68 | 2.13 | 67 | 0.02 | 15.71 | 2.15 | 68 | 0.02 |
| Comp. Ex. 3 | 15.65 | 2.81 | 213 | 0.02 | 13.69 | 3.47 | 284 | 966 |

In Table 3, ESR represents an equivalent series resistance at 100 kHz, and each value is the average for 10 samples, respectively.

As shown in Table 3, the characteristics of the capacitor of the present invention did not show any significant change even after the soldering process. On the other hand, the characteristics of the capacitor of the Comparative Example 3 showed a significant deterioration in the solid electrolyte caused by the soldering process.

EXAMPLE 9

Into an aluminum case (3 mmφ) was charged 17 mg of the complex obtained in Example 1, and this was heated at 340° C. until being melted. A preheated winding type aluminum electrolytic capacitor unit having a positive film-forming aluminum having an anodized surface, a negative collector and separating paper (see FIGS. 11 and 12) was impregnated with the melted complex, then the impregnated unit was removed from the aluminum case and cooled to obtain a solid electrolytic capacitor. After being connected with extended electrode ends, the whole impregnated unit was sealed with resin, and the extended ends kept free from the resin were bent under the bottom of the body, respectively. Thus, chip-type solid electrolytic capacitors were obtained as shown in FIG. 13, FIG. 14 and FIG. 15.

The current leakage of the chip-type capacitor the unit of which was rated at 16 V and 1 μF was reduced by applying a voltage of 16 V at 105° C.

The initial characteristics of this chip-type capacitor and its high temperature load characteristics after being subjected to a temperature of 105° C. for 1000 hours for the lying type as shown in FIG. 13 are summarized in Table 4. These values were the average for 10 samples.

The chip-type capacitor was also dipped into the solder bath maintained at 260° C. for 10 seconds. The characteristics of the chip-type capacitor before and after subjection to the test are shown in Table 5.

EXAMPLE 10

The experiment of Example 9 was repeated for the complex obtained in Example 2. The result of the test to measure its high temperature load characteristics is summarized in Table 4. And the result of the test to measure the effect of soldering is shown in Table 5.

COMPARATIVE EXAMPLE 4

The experiment of Example 9 was repeated for the complex obtained in the Comparative Example 3. The result of the test to measure its high temperature load characteristics is summarized in Table 4. And the result of the test for the soldering is shown in Table 5.

TABLE 4

| | Initial value | | | | Value after 1000 hours at 105° C. | | | |
|---|---|---|---|---|---|---|---|---|
| | Cap (μF) | tan δ (%) | ESR (mΩ) | LC/60" (μA) | Cap (μF) | tan δ (%) | ESR (mΩ) | LC/60" (μA) |
| Ex. 9 | 1.035 | 1.30 | 468 | 0.02 | 1.018 | 1.37 | 476 | 0.02 |
| Ex. 10 | 1.031 | 1.34 | 217 | 0.02 | 1.027 | 1.40 | 223 | 0.02 |
| Comp. Ex. 4 | 1.007 | 2.26 | 1232 | 0.02 | 0.843 | 5.71 | 1959 | 0.07 |

As shown in Table 4, the characteristics of the chip-type capacitor of the present invention are superior to those of the Comparative Example 4, especially with regard to its high temperature load characteristics, this implies that the chip-type capacitor of the present invention has excellent thermal stability and life characteristics. Similar results were also obtained for the standing type as shown in FIG. 14, and for the lying type in FIG. 15.

TABLE 5

| | Initial value | | | | Value after soldering test | | | |
|---|---|---|---|---|---|---|---|---|
| | Cap (μF) | tan δ (%) | ESR (mΩ) | LC/60" (μA) | Cap (μF) | tan δ (%) | ESR (mΩ) | LC/60" (μA) |
| Ex. 9 | 1.037 | 1.29 | 462 | 0.02 | 1.036 | 1.28 | 459 | 0.02 |
| Ex. 10 | 1.033 | 1.32 | 218 | 0.02 | 1.034 | 1.33 | 220 | 0.02 |
| Comp. Ex. 4 | 1.005 | 2.25 | 1236 | 0.02 | 0.988 | 3.92 | 1472 | 87.4 |

As shown in Table 5, the excellent characteristics of the chip-type capacitor are maintained even after the soldering process. On the other hand, the capacitor of Comparative Example 4 showed a significant deterioration of the solid electrolyte caused by the soldering process. Similar results were also obtained for the standing type as shown in FIG. 14 and the lying type in FIG. 15.

EXAMPLES 11, 12 AND COMPARATIVE EXAMPLE 5

Figure 17:
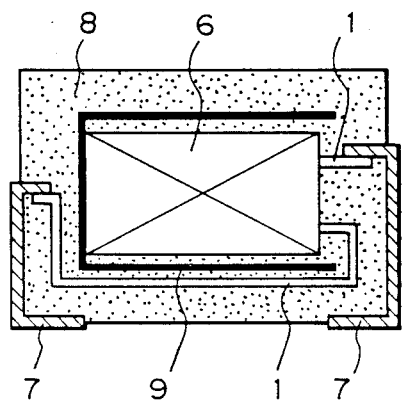
Figure 18:
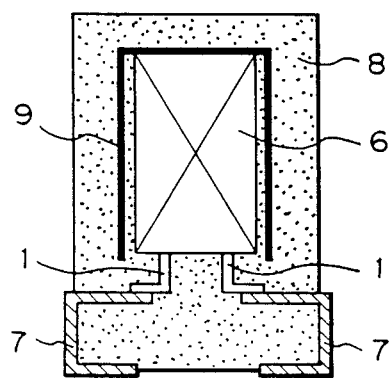

The experiments of Examples 9, 10 and Comparative Example 4 were repeated except that without being removed from the aluminum case. The impregnated unit was cooled and sealed with resin together with the aluminum case. Thus chip-type solid electrolytic capacitors were obtained as shown in FIG. 16, FIG. 17 and FIG. 18.

Figure 16:
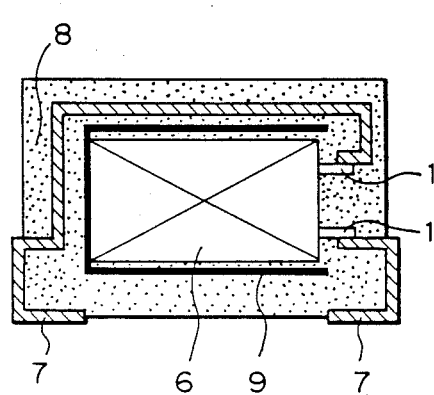

The characteristics of the lying type as shown in FIG. 16 before and after subjection to the soldering test are shown in Table 6.

TABLE 6

|  | Initial value | | | | Value after soldering test | | | |
| --- | --- | --- | --- | --- | --- | --- | --- | --- |
|  | Cap ($\mu$F) | tan $\delta$ (%) | ESR (m$\Omega$) | LC/60" ($\mu$A) | Cap ($\mu$F) | tan $\delta$ (%) | ESR (m$\Omega$) | LC/60" ($\mu$A) |
| Ex. 11 | 1.052 | 1.25 | 447 | 0.02 | 1.048 | 1.23 | 445 | 0.02 |
| Ex. 12 | 1.048 | 1.29 | 211 | 0.02 | 1.045 | 1.28 | 210 | 0.02 |
| Comp. Ex. 5 | 1.014 | 2.20 | 1205 | 0.02 | 0.996 | 3.89 | 1460 | 85.7 |

As shown in Table 6, the superior characteristics of the chip-type capacitor of this invention are once again proved.

Similar results were also obtained for the lying type as shown in FIG. 17 and for the standing type in FIG. 18.

EXAMPLES 13, 14 AND COMPARATIVE EXAMPLE 6

Figure 19:
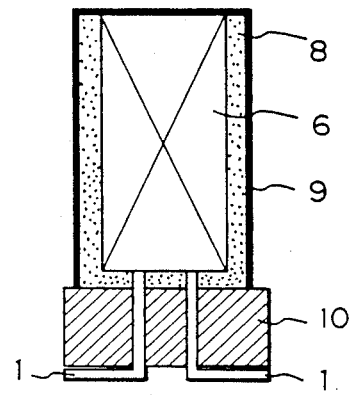

Examples 11, 12 and Comparative Example 5 were repeated except that the sealing with resin was carried out only inside the aluminum case, and two electrodes were bent to the bottom of the heat-resisting resin as shown in FIG. 19.

The characteristics of the standing type as shown in FIG. 19 before and after subjection to the soldering test are shown in Table 7.

TABLE 7

|  | Initial value | | | | Value after soldering test | | | |
| --- | --- | --- | --- | --- | --- | --- | --- | --- |
|  | Cap ($\mu$F) | tan $\delta$ (%) | ESR (m$\Omega$) | LC/60" ($\mu$A) | Cap ($\mu$F) | tan $\delta$ (%) | ESR (m$\Omega$) | LC/60" ($\mu$A) |
| Ex. 13 | 1.051 | 1.23 | 450 | 0.02 | 1.050 | 1.22 | 440 | 0.02 |
| Ex. 14 | 1.045 | 1.30 | 210 | 0.02 | 1.047 | 1.28 | 212 | 0.02 |
| Comp. Ex. 6 | 1.009 | 2.21 | 1200 | 0.02 | 0.991 | 3.85 | 1400 | 81.4 |

As shown in Table 7, the superior characteristics of the chip-type capacitor of this invention are clearly obvious.

As can be understood from the above, the charge transfer complex of the present invention comprising N,N'-alkylene-di-3,5-lutidine as a donor has remarkable thermostability, the solid electrolytic capacitor comprising said complex has excellent high temperature load characteristics and excellent resilience characteristics, and finally the chip-type solid electrolytic capacitor is accomplished by using said charge transfer complex.

What is claimed is:

1. A charge transfer complex comprising N,N'-alkylene-di-3,5-lutidine as a donor and 7,7,8,8-tetracyanoquinodimethane as an acceptor, the molar ratio of the acceptor to the donor of the charge transfer complex being between 3.0 and 5.0.

2. The charge transfer complex according to claim 1, wherein the number of carbon atoms of said alkylene of N,N'-alkylene-di-3,5-lutidine as a donor is between 1 and 12.

3. A process for preparation of a charge transfer complex comprising the steps of:
   (a) reacting alkylenediiodide and 3,5-lutidine to react with each other in an organic solvent under reflux or in the absence of solvent; and
   (b) reacting the product obtained by said reaction and 7,7,8,8-tetracyanoquinodimethane to react with each other in an organic solvent under reflux.

4. The process according to claim 3, wherein the solvent used for the latter reaction (step b) is acetonitrile.

5. A solid electrolytic capacitor comprising a capacitor unit impregnated a charge transfer complex as an electrolyte which has N,N'-alkylene-di-3,5-lutidine as a donor and 7,7,8,8-tetracyanoquinodimethane as an acceptor, the molar ratio of the acceptor to the donor of the charge transfer complex being between 3.0 and 5.0.

6. The solid electrolytic capacitor according to claim 5, wherein the capacitor unit is a winding type consists of an aluminum anode having anodized surface on the aluminum plate, aluminum cathode and spacer between them.

7. The solid electrolytic capacitor according to claim 5, wherein the number of carbon atoms of said alkylene of N,N'-alkylene-di-3,5-lutidine as a donor is between 1 and 12.

8. The solid electrolytic capacitor according to claim 7, wherein the said molar ratio is between 3.5 and 4.5.

9. The solid electrolytic capacitor according to claim 5, wherein the type of the capacitor is a chip-type.

* * * * *

UNITED STATES PATENT AND TRADEMARK OFFICE
CERTIFICATE OF CORRECTION

PATENT NO. : 4,982,312
DATED : January 1, 1991
INVENTOR(S) : Shuko Shindo et al.

It is certified that error appears in the above-identified patent and that said Letters Patent is hereby corrected as shown below:

ON THE TITLE PAGE

[75] Inventors, change "Gunma" to --Gunma-ken--.

Column 1, line 18, after "large-capacity" insert --and--.
Column 2, line 11, change "above-mentioned" to --mentioned above--.
Column 2 line 16, change "above-mentioned" to --mentioned above--.
Column 3, line 9, change "at" to --an--.
Column 5, line 10, change "di3" to --di-3--.
Column 5, line 10, after "was" insert --found--.
Column 6, line 25, change "mmø" to --mm°--.

Column 6, line 25, after "impregnated" insert --with--.

Signed and Sealed this

Eighteenth Day of February, 1992

Attest:

HARRY F. MANBECK, JR.

*Attesting Officer*     *Commissioner of Patents and Trademarks*